United States Patent [19] [11] Patent Number: 4,641,668
Namekawa [45] Date of Patent: Feb. 10, 1987

[54] ULTRASONIC BLOOD FLOW IMAGING METHOD AND APPARATUS

[75] Inventor: Koroku Namekawa, Mitaka, Japan

[73] Assignee: Aloka Co., Ltd., Tokyo, Japan

[21] Appl. No.: 767,148

[22] Filed: Aug. 19, 1985

Related U.S. Application Data

[63] Continuation-in-part of Ser. No. 516,792, Jul. 25, 1983, abandoned.

[30] Foreign Application Priority Data

Jul. 28, 1982 [JP] Japan .............................. 57-130503

[51] Int. Cl.4 ............................................. A61B 10/00
[52] U.S. Cl. ...................................... 128/663; 358/82
[58] Field of Search ................................... 358/81–82, 358/514

[56] References Cited

U.S. PATENT DOCUMENTS

| 3,307,142 | 2/1967 | Doebler | 367/110 X |
| 3,617,997 | 11/1971 | Maass et al. | 367/110 |
| 3,711,822 | 1/1973 | Muller | 367/110 X |
| 4,125,858 | 11/1978 | Hounsfield et al. | 358/82 |
| 4,183,046 | 1/1980 | Dalke et al. | 358/22 |
| 4,415,922 | 11/1983 | Raymond et al. | 358/22 |
| 4,543,826 | 10/1985 | Ferrari | 128/660 X |

OTHER PUBLICATIONS

White, D. N. et al., "Color Coded Differential Velocity Corotid Bifurcation Scanner", 1976 UTS Symp. Proceedings, Annapolis, Md. (Sep. 29–Oct. 1, 1976), pp. 85–87.
Sams Color TV Training Manual, Howard Sams Company, Indianapolis, Ind., 1971, pp. 13, 15.

Primary Examiner—Kyle L. Howell
Assistant Examiner—Francis J. Jaworski
Attorney, Agent, or Firm—Koda and Androlia

[57] ABSTRACT

An ultrasonic blood flow imaging method for two-dimensionally displaying the velocity distribution of blood flow within a body to be examined is characterized in that the velocity distribution is displayed as a color picture in which the velocity direction is represented by one color when positive and by another different color when negative, and the magnitude of the velocity is represented by varying the brightness of the color concerned. An ultrasonic imaging apparatus for carrying out this method comprises an ultrasonic transmitter/receiver which outputs a tomographic image signal corresponding to a specific region of an object, and an average velocity signal and a velocity deviation signal corresponding to the velocity of blood flow within the specified region. These signals are stored in respective frame memories and then processed by a color processor to produce a color video signal which is input to a color display for displaying a tomographic image, and the velocity and velocity deviation of the blood flow.

3 Claims, 5 Drawing Figures

ULTRASONIC BLOOD FLOW IMAGING METHOD AND APPARATUS

This is a continuation-in-part of Ser. No. 516,792 filed July 25, 1983 now abandoned.

BACKGROUND OF THE INVENTION

1. Field of the Invention

This invention relates to an ultrasonic blood flow imaging method and apparatus, and more particularly to such a method and apparatus capable of two-dimensionally displaying the velocity distribution of blood flow in a body to be examined.

2. Prior Art

There are known ultrasonic imaging methods wherein an ultrasonic wave beam is directed into an object to be examined and an image is formed using the reflected echo produced as a result of differences in acoustic impedance within the object. These methods are advantageous in that they make it possible to observe the interior of an object without adversely affecting its structural make-up and are therefore used, for example, in diagnostic examination of afflicted tissues and organs in humans. These methods have been applied in ultrasonic diagnostic apparatuses and the like.

A more sophisticated utilization of ultrasonic waves developed in recent years is the pulse-doppler method, wherein the doppler effect that arises when an ultrasonic pulse beam strikes blood flow in a body to be examined is used to determine the velocity of the blood flow. This method has been successfully applied in, for example, blood flow velocity meters.

Although this velocity distribution has conventionally been displayed as a black-and-white image, it has, with the devices used for this purpose, been difficult to represent the two-dimensional distribution accurately. Thus, proposals have been made to improve the situation by use of color imaging method.

The principle of the conventional imaging method is shown in FIG. 1. When the signal representing the movement of the blood flow varies periodically as shown in the figure, six colors (a,b,c,d,e and f) are assigned one each for six velocity bands in the positive direction and six colors (h–m) are assigned for six velocity bands in the negative direction. In this way, colors can be displayed to correspond to the velocity distribution. This conventional system has the advantage of making it possible to judge the velocity distribution of a glance from the colors displayed. On the other hand, however, although this conventional method provides a very clear picture when the velocity of the blood flow remains constant, it has the disadvantage that the colors mix to produce a picture that is hard to read when the velocity and the direction of the blood flow rapidly varies, especially in blood flow of the heart. This method is also disadvantageous in a case like that shown in FIG. 2 where the change with time is not regular and local portions exhibit large deviations within the overall blood flow movement, since in such cases the colors mix throughout the picture making it difficult to read the picture and almost totally impossible to interpret those portions where the positive and the negative directions of blood flow are intermingled.

SUMMARY OF THE INVENTION

The object of the present invention is to provide an improved ultrasonic blood flow imaging method and apparatus which are capable of producing a two-dimensional color display of velocity distribution of blood flow that is exceedingly easy to read.

This object of the present invention is attained by providing an ultrasonic blood flow imaging method for two-dimensionally displaying the velocity distribution of blood flow of a body to be examined, which method is characterized by the positive and negative velocity directions being represented by different colors and the velocity of the blood flow being represented by the brightness of the respective colors.

DETAILED DESCRIPTION OF THE INVENTION

Figure 3:
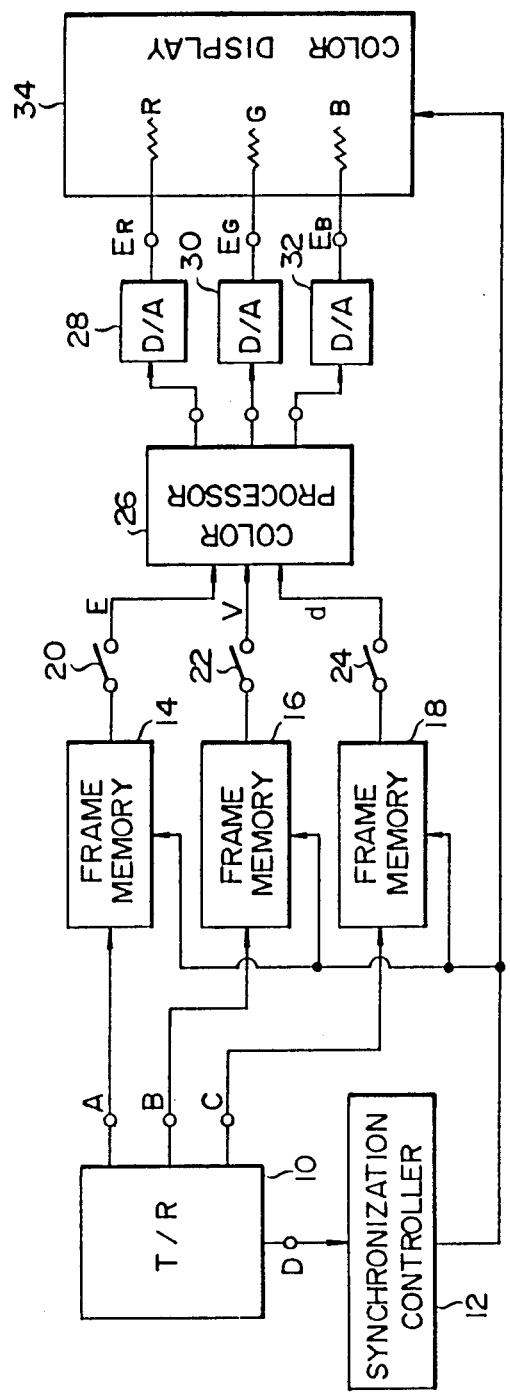
FIG. 3 is a block diagram of the circuit of an ultrasonic diagnostic apparatus employing the ultrasonic blood flow imaging method according to this invention.

FIG. 3 shows an embodiment of the present invention as applied to an ultrasonic diagnostic apparatus for producing a tomograph of a desired portion of a human body. This ultrasonic diagnostic apparatus produces a black-and-white B-mode tomograph having superposed thereon the velocity distribution of blood flow as determined by the pulse-doppler method.

An ultrasonic transmitter/receiver 10 uses an ultrasonic beam to produce a B-mode tomographic signal. Moreover, through the transmission and reception of an ultrasonic pulse beam, it is possible to obtain a blood velocity distribution signal for the blood flow within the plane of the aforesaid B-mode tomograph. That is to say, in the embodiment the ultrasonic transmitter/receiver 10 consists of a combination of an ordinary B-mode echo device and an ultrasonic doppler device and produces the tomograph by either linear or sector electronic scanning.

The ultrasonic transmitter/receiver 10 produces three separate signals. The first signal output from terminal A is a tomographic signal, more specifically a B-mode tomographic signal representing a desired tomographic plane. The second signal output from terminal B is a velocity signal produced by the pulse-doppler method, more specifically an average blood flow velocity signal. The third signal output from terminal C is a deviation signal, one kind of velocity signal according to the pulse-doppler method, which includes information on the deviation of the instantaneous velocity from the average velocity. For this third signal is used, for example, one with a dispersion value corresponding to the standard deviation or to the square of the standard deviation.

The aforesaid three signals are produced as digital signals within the transmitter/receiver 10 by conversion from the analog reflection echo signal. The transmitter/receiver 10 also outputs from terminal D a transmission repetition pulse, a clock pulse or an address signal corresponding to the direction of transmission/reception of the ultrasonic beam. The signal from the terminal D is fed to a synchronization controller 12 which produces a synchronization signal required for memory operation and display as will be explained later.

The three signals from the transmitter/receiver 10 are written into respective frame memories 14, 16, 18 and the addresses at which these signals are written is determined by the synchronization signal from the synchronization controller 12. Therefore, tomographic, average velocity and deviation signals for the tomographic plane are respectively stored at the same addresses in the frame memories 14, 16, 18.

The data stored in the frame memories 14, 16, 18 are supplied to a color processor 26 through selector switches 20, 22, 24. The selector switches 20, 22, 24 are ON/OFF controlled so as to include only desired portions of the detected data in the video display.

The color processor 26 converts the input data into color video signals in accordance with a prescribed processing method. In this embodiment, color processor 26 processes and outputs three color video signals corresponding respectively to three primary colors: red (R), green (G) and blue (B). These three color video signals are supplied to the input terminal of a color display 34 through D/A converters 28, 30, 32. In the embodiment, the color display 34 is a color CRT tube to which the D/A converters 28, 30, 32 supply R, G and B inputs respectively.

As the synchronization signal from the synchronization controller 12 is supplied to the color display 34 as sweep input, the color display 34 is able to display the data stored at specific addresses in the frame memories 14, 16, 18 as a two-dimensional color image.

The present invention is characterized by the fact that the color display 34 displays the velocity distribution two-dimensionally in color, the color image displayed in the case of the embodiment being that of a combination of the average blood flow velocity and the deviation therefrom.

When the RGB inputs applied to the display 34 are of equal voltage, the color displayed is white. This white display is varied in brightness in accordance with the variation in brightness input at this time, so that the desired tomograph is displayed in black and white.

Therefore, if only the selector switch 20 is on or if the transmitter/receiver 10 produces only a tomographic signal, the B-mode tomograph will be displayed on the color display 34 in white.

Next, in respect of the average flow velocity data from the frame memory 16, the color processor 26 specifies one or the other of two predetermined colors depending on whether the velocity is positive or negative and also varies the brightness of the specified color in accordance with the velocity data at that time. The positive and negative directions of movement of the blood flow are defined in advance, as by calling velocities which bring the moving member closer to the probe which sends and receives the beam in accordance with the pulse-doppler method to be positive and velocities which move it away therefrom to be negative. Thus, the velocity data stored in the frame memory 16 includes both the magnitude of the velocity and its sign (positive or negative) for each time of measurement. Here, denoting the velocity data as V and the voltages applied to the R, G and B terminals of the color display 34 as $E_R$, $E_G$ and $E_B$, the color processor 26 carries out the operations indicated by the following formulas on the average blood flow velocity data.

In the case where the average flow velocity is positive:

$$E_R = krV$$

$$E_G = kgV$$

$$E_B = 0$$

And in the case where the average flow velocity is negative:

$$E_R = 0$$

$$E_G = kgV$$

$$E_B = kbV$$

(where kr, kg, kb are constants).

From the foregoing explanation, it will be understood that based on the average flow velocity data stored in the frame memory 16 the color processor 26 mixes red and green to produce yellow in the case where the velocity is positive and mixes blue and green to produce bluish-green in the case where the velocity is negative and that in either case the brightness of the color concerned is varied in proportion to the velocity.

When, as in the embodiment described above, positive velocity is indicated by a warm color (yellow) and negative velocity is indicated by a cool color (bluish-green), it becomes very easy to distinguish positive and negative velocities. Moreover, as velocity magnitude is represented by varying the brightness of the color concerned, much less effort is needed to distinguish velocities than is required in the conventional method in which a different color is used to represent each velocity band. In particular, the method of this invention makes it possible to obtain an exceedingly good two-dimensional color representation in a case where the blood flow in the object under examination makes rapid, irregular movements, for example in the case of the heart.

As will be clear from the foregoing explanation, in accordance with the present invention, one of two colors is selected depending on whether the movement of the blood flow within the body under examination is fundamentally positive or negative.and, therefore, only one of the two colors appears on the screen at any one time. Consequently, as there is no possibility of other colors interfering, it is possible to realize a tremendous improvement over the conventional method which produces an unpleasant picture with complexly intermixed colors.

It is preferable for the two selected colors to contrast as strongly as possible in order to give a strong impression of "positive" and "negative." Specifically, it is best to choose colors that give totally opposite impressions such as the yellow and bluish-green used in this embodiment. These two contrasting colors are perceived very differently, one as a warm color and the other as a cool color, making them very easy to distinguish and making the resulting picture very easy to view.

Moreover, in this invention, velocity is represented by variation in the brightness of the color concerned, with the brightness increasing in proportion as the velocity increases. Because of this, velocity information, particularly the average flow velocity etc., can be displayed in a very easy-to-read form. In the embodiment described above, not only the average flow velocity but also any velocity deviations at this time can be simultaneously displayed two-dimensionally in color so that even when the velocity and direction of the blood flow, for example, in heart blood flow, varies complexly, it is possible to display these complex variations in the two-dimensional picture.

Figure 1:
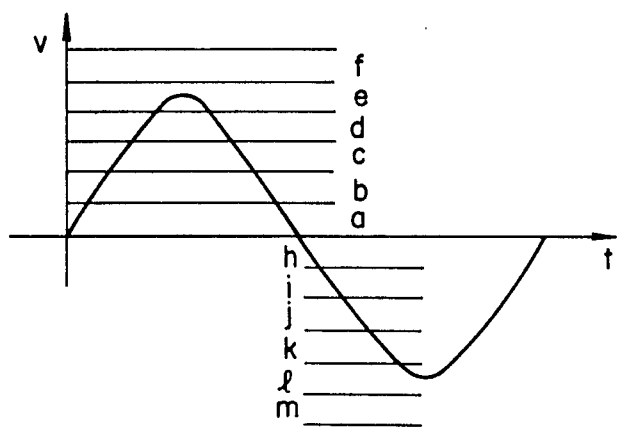
FIGS. 1 and 2 are diagrams for explaining conventional color display systems.
Figure 2:
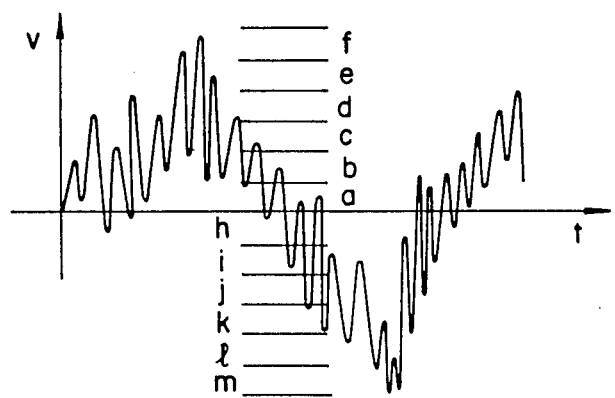
Figure 4:
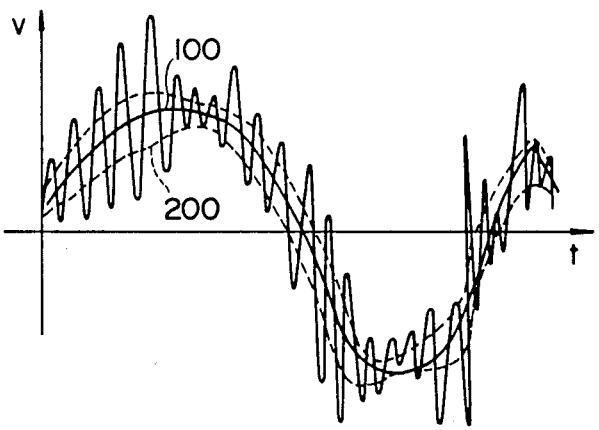
FIG. 4 is a diagram for explaining the operation of the preferred embodiment according to the invention described in FIG. 3.

FIG. 4 shows the relation between the average blood flow velocity and velocity deviations in this invention. The solid-line curve 100 indicates the average flow velocity. As explained above, the display is made in yellow when this average flow velocity 100 is positive and is made in bluish-green when it is negative. The broken-line curves 200 in FIG. 4 indicate deviation from the respective average flow velocities and this deviation is represented in color according to the size of the broken-line band.

In this embodiment, it is possible to represent the magnitude of deviation by blending another prescribed color with the color indicating positive or negative velocity in such a way that the previously fixed color indicating the average flow velocity is changed by having the prescribed color blended therewith in a degree corresponding to the magnitude of the deviation. In the embodiment, deviation is represented by varying the amount of green mixed into the yellow for positive velocity and into bluish-green for indicating negative velocity. In other words, whereas in the representation of only the average flow velocity the values of kr, kg and kb all maintain constant values, in the representation of deviation the value of kg corresponding to green is, in this embodiment, varied according to the deviation.

More specifically, when the deviation value stored in frame memory 18 is small, kg is small; when the deviation becomes large, kg becomes large; and when the deviation is minimum, that is when the instantaneous flow velocity and the average flow velocity are equal, kg becomes zero. In this case, the display becomes red when the velocity is positive and becomes blue when the velocity is negative. Moreover, when the deviation value reaches a prescribed maximum value, the value of kg becomes equal to the aforesaid set value of the average flow velocity alone and, as a result, the positive display becomes yellow and the negative display becomes bluish-green. Thus, in considering the deviation, depending on the magnitude of the deviation, the mixing of colors takes place over a range extending from red to yellow in the case of positive velocity and over a range extending from blue to bluish-green in the case of negative velocity so that it is possible to read the deviation from the color mixture displayed.

Thus, in accordance with this invention, the blood velocity information is displayed in one or the other of two colors depending on the direction of the velocity and the magnitude of the velocity is displayed as the brightness of the color concerned so that the velocity information can be read most clearly. Moreover, as in the embodiment, the velocity information and the deviation information can be displayed independently or together as desired and as the changes in velocity and the changes in deviation are represented as changes within the same color system, it is possible to distinguish the changes in the picture with ease.

Further, when the information pertaining to the blood flow is displayed as superposed on the image of the surrounding stationary part in the manner of this embodiment, it becomes most easy to grasp the interrelation between the blood flow and stationary part. In particular, when this invention is used in conjunction with an ultrasonic diagnostic apparatus or the like, it becomes possible to observe the flow of blood etc. within an organ with reference to a tomograph thereof and thus to obtain a huge quantity of diagnostic data.

It should be noted that although in the embodiment described the average blood flow velocity is displayed alone in yellow or bluish-green, it is also possible to select other colors as desired. For example, it is possible in displaying only the average flow velocity to eliminate the signal for displaying green and to use only the two colors red and green.

Although it is possible to use an ordinary arithmetic circuit for the color processor 26, it is preferable to further provide a ROM for storing the predetermined condition of the processing operation so that processing can be carried out at a high speed.

Figure 5:
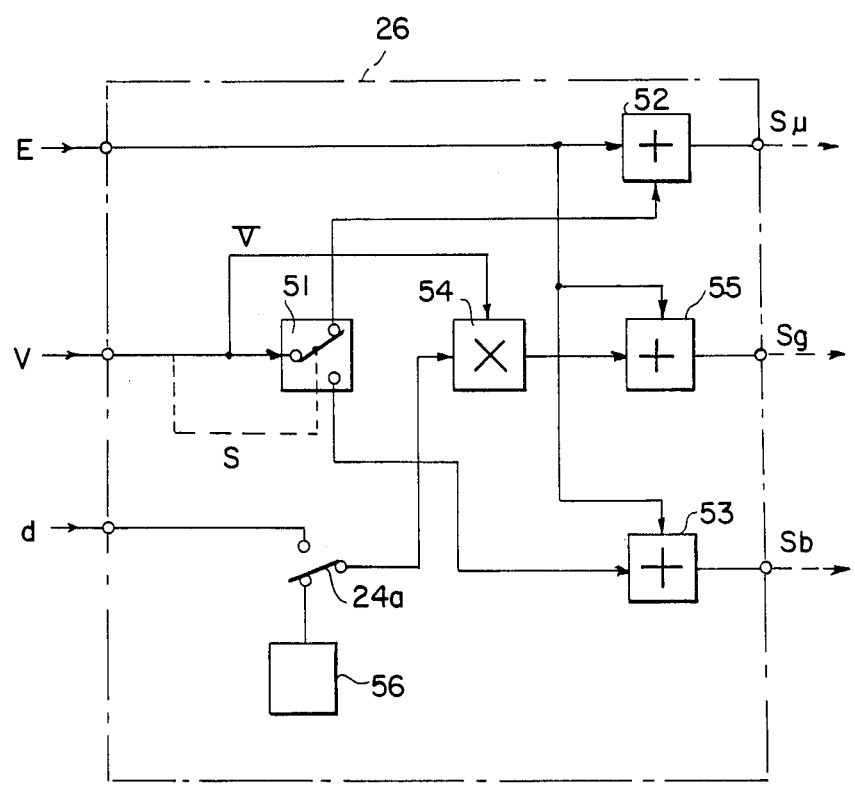
FIG. 5 is a block diagram showing the circuit of the color processor.

Referring to FIG. 5, shown therein is a block diagram showing the circuit of the color processor 26. In the FIG. 5, the three input signals supplied from the selector switches 20, 21 and 22 shown in FIG. 3 are an acho signal E representing the tomographic image, an average velocity V, and a deviation signal d. These signals have been converted into digital signals, and because of quantization error involved, the minute echo level and low velocity are shown as zero.

Since the velocity takes positive and negative values, it is composed of a numeric bit representing the absolute value and a directional bit representing the positive and the negative. The directional bit is 1 when it is positive, and 0 when negative. The average verocity V is separated into the absolute value $|V|$ and the directional signal S in the color processor 26. The directional signal S puts the data selector 51 in work. When the directional signal S is 1, the data selector 51 supplies the absolute value $|v|$ to an adder 52. When the directional signal S is 0, the data selector 51 supplies the absolute value $|V|$ to an adder 53. As a result, when the average velocity V is positive, the output Sr from the adder 52 can be shown by the equation below:

$$Sr = |V| + E \tag{1a}$$

In the same manner, when the average velocity V is negative, the output Sb of the adding means 53 can be shown by:

$$Sb = |V| + E \tag{1b}$$

A selector switch 24a works together with the selector switch 24 of FIG. 3. When the deviation signal d is being inputted into the selector switch 24a, it supplies the deviation signal d to multiplier 54. Into this multiplier 54 is also supplied with the absolute value $|V|$. The output of the multiplier is further added to the echo signal E in the adder 55. As a result, the output Sg of the adder 55 is shown as follows:

$$Sg = d \cdot |V| + E \tag{1c}$$

The deviation signal d takes the value of 0–1. When the deviation signal d is not being supplied, instead of this deviation signal, the numeric value 1 from the numeric value generator 56 is supplied into the adder 54. Therefore, the equation (1c) is:

$$Sg = |V| + E \tag{1d}$$

Outputs Sr, Sg, and Sb are converted into analogue voltages by analogue-digital converters 28, 30 and 32.

These voltage values are adjusted in accordance with color sensitivity or CRT and then become grid voltages Er, Eg, and Eb. When, in this case, the signal-voltage conversion constants are Kr, Kg, and Kb, the previous equations (1a), (1b), and (1d) are shown as:

$$E_R = Kr \cdot |V| + Kr \cdot E \quad (2a)$$

$$E_B = Kb \cdot |V| + Kb \cdot E \quad (2b)$$

$$E_G = Kg \cdot d |V| + Kg \cdot E \quad (2c)$$

$$E_G = Kg \cdot |V| + Kg \cdot E \quad (2d)$$

When the echo signals from the tissues, which do not move or move slowly, are being received, there is normally no blood, and V=0. Therefore, the equations are:

$$E_R = Kr \cdot E \quad (3a)$$

$$E_B = Kb \cdot E \quad (3b)$$

$$E_G = Kg \cdot E \quad (3c)$$

In this case, the constants Kr, Kb, and Kg are determined so that the images on the CRT are white. As a result, the images of the tissues are shown white.

On the other hand, the echo signals from the tissue where the blood flows all the time, such as inside the heart, blood vessel, etc., are very weak or cannot be received, and E=0. Therefore, the equation (2) is shown as follows:

$$E_B = 0 \quad (4a)$$

$$E_R = Kr \cdot |V|$$

$$E_G = Kg \cdot d \cdot |V|$$

$$(V > 0)$$

$$E_B = Kb \cdot |V| \quad (4b)$$

$$E_G = Kg \cdot d \cdot |V|$$

$$E_R = 0$$

$$(V < 0)$$

Since the data of blood is always shown by only two colors, the color white does not appear. As a result, the data of the blood is clearly distinguished from the images of the tissues.

As shown by the equation (4), the color green changes in accordance with the product obtained by multiplying the velocity |V| and the deviation d. The ratio of the two colors can be shown as follows from the equation (4):

$$E_G/E_R = Kg \cdot d/Kr \ (V>0) \quad (5a)$$

$$E_G/E_B = Kg \cdot d/Kb \ (V<0) \quad (5b)$$

More specifically, the mixing ratio of the two colors, that is, the hue, is determined only by the deviation d. This is because Kr, Kg, and Kb are fixed numbers.

Within the same hue, the brightness proportions to velocity; therefore, the velocity and the deviation can be shown simultaneously. For instance, when the deviation is at the maximum, d equals 1. Therefore, the equations (4a) and (4b) become the same as those shown first. As a result, the positive velocity is shown in yellow, and the negative velocity in bluish-green (cyanogen). Furthermore, when the deviation d is at the minimum, that is, d is 0, the equations (4a) and (4b) are shown as follows:

$$E_R = Kr \cdot |V| \quad (6a)$$

$$E_G = 0$$

$$E_B = 0$$

$$(V > 0)$$

$$E_B = Kb \cdot |V| \quad (6b)$$

$$E_G = 0$$

$$E_B = 0$$

$$(V < 0)$$

As a result, the velocity is shown only as one color. In other words, the positive velocity is shown as red, and negative velocity is shown as blue. The brightness of the colors vary in proportion to the velocity.

Furthermore, by means of the equation (2), the tomographic image of the tissues, the blood velocity distribution and the deviation distribution can be superposed on the CRT.

Further, it should be noted that it is not absolutely necessary to provide the selector switches described in connection with the above embodiment although these switches are convenient since they make it possible to combine the information from the frame memories in various ways.

Furthermore, widely used conventional color-TV and VTR can be used to display the color image by reading out the output signals from the frame memories 14, 16 and 18 in synchronizing manner to scanning signals for the color-TV and VTR.

Again, although in the embodiment described the output of the color processor is used to control the grid voltage of a color picture tube, it is possible instead to use it to phase modulate a sub-carrier as in an ordinary television set and then to use the demodulation voltage thereof to control the RGB voltage.

As will be clear from the foregoing, this invention makes it possible to effectively utilize a color display device to obtain a two-dimensional display of the velocity distribution of a blood flow within a body under examination and, in particular, makes it possible to obtain a very easily readable display even when the moving member moves rapidly.

I claim:

1. In an ultrasonic blood flow imaging method for displaying the spatial velocity distribution of blood flow within a body under examination, the improvement comprising the steps of:

displaying a first function of the spatial velocity distribution of blood flow as a color picture wherein said first function direction is represented by one color when positive and by another different color when negative;

mixing at least one further color in accordance with a second function of the spatial velocity distribution of blood flow representative of a deviation from said first function in proportion to the magnitude of said second function with said at least one further color selected depending on whether the blood flow is positive or negative, whereby the said second function is represented by a change in color in said color picture; and representing the magnitude of said first function by varying the brightness of the color displayed in said color picture.

2. An ultrasonic blood flow imaging method according to claim 1, further comprising the step of displaying stationary portions in the vicinity of the blood flow in white as superposed on the color picture of said first function of spatial velocity distribution.

3. An ultrasonic imaging apparatus for imaging blood flow and tomographic signals comprising an ultrasonic transmitter/receiver means for outputting a tomographic image signal produced by sending an ultrasonic beam into a specific region of a body under examination and electrically detecting the reflected echo from said region, and including pulse doppler means for selectively detecting a signal representative of a first function of the spatial velocity distribution of blood flow and a second signal representative of a second function of spatial velocity distribution of blood flow and of a deviation from said first function, said signals corresponding to the velocity of movement of blood flow within said region; a plurality of frame memory means coupled to said transmitter/receiver for storing each of said signals; a color processor means coupled to said frame memory means for producing a color video signal from said signals stored in said frame memory means; and a color display means responsive to said color video signal from said color processor means for displaying a tomographic image of said region in white, for displaying the direction of said first function within said region in one color when positive and in another different color when negative, and for displaying the magnitude of said first function by varying the brightness of the color displayed, and further for displaying said tomographic image and said first and second functions superposed one on the other, said color processor means further comprising means for mixing at least one further color with the color displayed depending on the magnitude of said second function.

* * * * *